(12) United States Patent
Martin

(10) Patent No.: US 6,376,485 B1
(45) Date of Patent: Apr. 23, 2002

(54) BENZOXAZOLES WITH PDE-INHIBITING ACTIVITY

(75) Inventor: Thomas Martin, Constance (DE)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/720,812

(22) PCT Filed: Jun. 26, 1999

(86) PCT No.: PCT/EP99/04451

§ 371 Date: Jan. 3, 2001

§ 102(e) Date: Jan. 3, 2001

(87) PCT Pub. No.: WO00/01695

PCT Pub. Date: Jan. 13, 2000

(30) Foreign Application Priority Data

Jul. 6, 1998 (EP) .............................. 98112469

(51) Int. Cl.⁷ ..................... A61K 31/42; C07D 413/04; C07D 263/56
(52) U.S. Cl. .................. 514/212.08; 514/321; 514/375; 540/524; 546/198; 548/217; 548/224
(58) Field of Search ............................ 514/212.08, 321, 514/375; 540/524; 546/198; 548/217, 224

(56) References Cited

U.S. PATENT DOCUMENTS 4,405,633 A * 9/1983 Brown et al. ............... 424/272

FOREIGN PATENT DOCUMENTS

EP 0127066 A2 * 5/1984
WO WO-96/11917 A1 * 4/1996

OTHER PUBLICATIONS

Gilchrist et al. Ring Contraction of 1,2,4–benzoxadiazines to benzoxazoles. J. Chem. Soc., Perkin Trans. 1, 1988, pp. 2169–2173.*

Nicholson et al., Differtial modulation of tissue function and therapeutic potential of selective inhibitors of cyclic nucleotide phosphodiesterase isoenzymes. TIPS, vol. 12, pp. 19–27, 1991.* de Brito et al., Type 4 phosphodiesterase inhibitors and their potential in the treatment of inflammatory disease. Emerging Drugs: The Prospect for Improved Medicines, Annual Executive Briefing 1997, Chapter 12, pp. 249–268.*

Bou et al., Investigation into three role of phosphodiesterase IV in bronchorelaxation, including studies with human bronchus. Br. J. Pharmacol., vol. 108, pp. 562–568, 1993.*

* cited by examiner

Primary Examiner—Brenda Coleman
(74) Attorney, Agent, or Firm—Jacobson Holman, PLLC

(57) ABSTRACT

Compounds of formula I

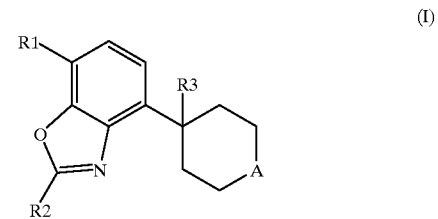

in which R1, R2, R3 and A have the meaning set forth in the specification, are selective cyclic nucleotide phosphodiesterase (PDE) inhibitors useful as therapeutics in human and veterinary medicine. They are distinguished by low toxicity, good enteral absorption (high bioavailability), a wide therapeutic breadth and absence of significant side effects.

9 Claims, No Drawings

BENZOXAZOLES WITH PDE-INHIBITING ACTIVITY

This application is a national stage entry under 35 U.S.C. 0371 of PCT/EP99/04451, filed Jun. 26, 1999 and published in English.

FIELD OF APPLICATION OF THE INVENTION

The invention relates to novel benzoxazoles which are employed in the pharmaceutical industry for the preparation of medicaments.

1. Known Technical Background

International Patent Application WO 96/11917 describes substituted benzoxazoles as cyclic nucleotide phosphodiesterase inhibitors of type 4. U.S. Pat. No. 4,405,633 and European Patent Application EP-A-127 066 propose substituted benzoxazoles as agents for the prevention and treatment of asthma.

2. Description of the Invention

It has now been found that the benzoxazoles described below in greater detail, which differ from the previously published compounds by a different type of substitution, have surprising and particularly advantageous properties.

The invention thus relates to compounds of the formula I

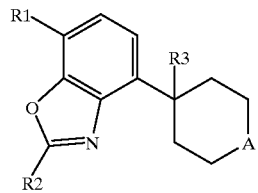

(I)

in which
- R1 is 1–6C-alkoxy, 3–7C-cycloalkoxy, 3–7C-cycloalkylmethoxy, benzyloxy or completely or predominantly fluorine-substituted 1–4C-alkoxy,
- R2 is hydrogen, 1–7C-alkyl, 3–7C-cycloalkyl, 3–7C-cycloalkylmethyl or 1–4C-alkoxy-1–4C-alkyl,
- R3 is hydrogen, hydroxyl, nitro, cyano, ethynyl, carboxyl, 1–4C-alkoxy or 1–4C-alkoxycarbonyl,
- A is B, —CH(R4)—, >C=O or >C=N—R5, where
  - B is oxygen (—O—), imino (—NH—), sulfinyl (—S(O)—), sulfonyl (—S(O)$_2$—) or carbonylimino (—C(O)NH—) and
  - R4 is hydroxyl, carboxyl, 1–4C-alkoxycarbonyl, aminocarbonyl, mono- or di-1–4C-alkylaminocarbonyl, hydroxyaminocarbonyl (—C(O)NHOH) or 1–4C-alkoxyaminocarbonyl,
  - R5 is hydroxyl or 1–4C-alkylcarbonyloxy, and the salts of these compounds.

1–7C-Alkyl represents straight-chain or branched alkyl radicals having 1 to 7 carbon atoms. Examples which may be mentioned are the heptyl, isoheptyl (5-methylhexyl), hexyl, isohexyl (4-methylpenty), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

1–6C-Alkoxy represents a radical which, in addition to the oxygen atom, contains a straight-chain or branched alkyl radical having 1 to 6 carbon atoms. Alkoxy radicals having 1 to 6 carbon atoms which may be mentioned are, for example, the hexyloxy, isohexyloxy (4-methylpentyloxy), neohexyloxy (3,3-dimethylbutoxy), pentyloxy, isopentyloxy (3-methylbutoxy), neopentyioxy (2,2-dimethylpropoxy), butoxy, isobutoxy, sec-butoxy, tert-butoxy, propoxy, isopropoxy, ethoxy and methoxy radicals.

3–7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy represents cyclopropylmethoxy, cyclobutylmethoxy, cyclopentylmethoxy, cyclohexyl-methoxy and cycloheptylmethoxy, of which cyclopropylmethoxy, cyclobutylmethoxy and cyclopentylmethoxy are preferred.

Completely or predominantly fluorine-substituted 1–4C-alkoxy which may be mentioned are, for example, the 2,2,3,3,3-pentafluoropropoxy, the perfluoroethoxy and the 1,2,2-trifluoroethoxy radicals, in particular the 1,1,2,2-tetrafluoroethoxy, the 2,2,2-trifluoroethoxy, the trifluoromethoxy and preferably the difluoromethoxy radicals.

3–7C-Cycloalkyl represents cyclopropyl, cyclobutyl, cyclopentyl, cyclohexyl and cycloheptyl, of which cyclopropyl, cyclobutyl and cyclopentyl are preferred.

3–7C-Cycloalkylmethyl represents a methyl radical which is substituted by one of the abovementioned 3–7C-cycloalkyl radicals. The 3–5C-cycloalkylmethyl radicals cyclopropylmethyl, cyclobutylmethyl and cyclopentylmethyl may preferably be mentioned.

1–4C-Alkoxy-1–4C-alkyl represents one of the abovementioned 1–4C-alkyl radicals which is substituted by one of the abovementioned 1–4C-alkoxy radicals. Examples which may be mentioned are the methoxymethyl and the methoxyetnyl radicals and the butoxyethyl radical.

1–4C-Alkoxycarbonyl represents a carbonyl group to which is bonded one of the abovementioned 1C-alkoxy radicals. Examples which may be mentioned are the methoxycarbonyl (CH$_3$O—C(O)—) and the ethoxycarbonyl (CH$_3$CH$_2$O—C(O)—) radicals.

In addition to the carbonyl group, mono- or di-14C-alkylaminocarbonyl radicals contain one of the abovementioned mono- or di-14C-alkylamino radicals. Examples which may be mentioned are the N-methyl, the N,N-dimethyl, the N-ethyl, the N-propyl, the N,N-diethyl and the N-isopropylaminocarbonyl radicals.

A 1–4C-alkylaminocarbonyl radical which may be mentioned is, for example, the methoxyaminocarbonyl radical (—C(O)NHOCH$_3$).

1–4C-Alkylcarbonyloxy represents a carbonyloxy group to which is bonded one of the abovementioned 1–4C-alkyl radicals. An example which may be mentioned is the acetoxy radical (CH$_3$C(O)—O—).

Suitable salts of compounds of the formula I—depending on substitution—are all acid addition salts or all salts with bases. Particular mention may be made of the pharmacologically tolerable salts of the inorganic and organic acids customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are also suitable. Examples of salts which bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which can initially be obtained as process products, for example in the preparation of the compounds according to the invention on an industrial scale, are converted into pharmacologically tolerable salts by processes known to the person skilled in the art.

It is known to the person skilled in the art that the compounds according to the invention and also their salts, when they are isolated, for example, in crystalline form, can contain various amounts of solvents. The invention therefore also includes all solvates and in particular all hydrates of the compounds of the formula I, and also all solvates and in particular all hydrates of the salts of the compounds of the formula I.

Compounds of the formula I to be emphasized are those in which
  R1 is 1–4C-alkoxy, 3–5C-cycloalkoxy or completely or predominantly fluorine-substituted 1–2C-alkoxy,
  R2 is 1–4C-alkyl, 3–5C-cycloalkyl, 3–5C-cycloalkylmethyl or 1–2C-alkoxy-1–2C-alkyl,
  R3 is hydroxyl, cyano, carboxyl, 1–2C-alkoxy or 1–2C-alkoxycarbonyl,
  A is B, —CH(R4)—, >C=O or >C=N—R5, where
    B is oxygen (—O—), sulfinyl (—S(O)—), sulfonyl (—S(O)$_2$—) or carbonylimino (—C(O)NH—) and
    R4 is hydroxyl, carboxyl, 14C-alkoxycarbonyl or aminocarbonyl,
    R5 is hydroxyl or 1–4C-alkylcarbonyloxy,
and the salts of these compounds.

Compounds of the formula I particularly to be emphasized are those in which
  R1 is 1–4C-alkoxy,
  R2 is 1–4C-alkyl or 3–5C-cycloalkyl,
  R3 is hydroxyl, cyano or methoxy,
  A is B, —CH(R4)— or >C=O, where
    B is oxygen (—O—) or sulfonyl (—S(O)$_2$—),
    R4 is hydroxyl, carboxyl, methoxycarbonyl or aminocarbonyl,
and the salts of these compounds.

One embodiment of the particularly preferred compounds of the formula I are those in which
  R1 is 1–4C-alkoxy,
  R2 is 1–4C-alkyl or 3–5C-cycloalkyl,
  R3 is hydroxyl, cyano or methoxy,
  A is B or —CH(R4)—, where
    B is oxygen (—O—) or sulfonyl (—S(O)$_2$—),
    R4 is carboxyl, methoxycarbonyl or aminocarbonyl,
and the salts of these compounds.

Preferred compounds of the formula I are those in which
  R1 is 1–4C-alkoxy,
  R2 is 1–4C-alkyl,
  R3 is cyano,
  A is B, —CH(R4)— or >C=O, where
    B is oxygen (—O—) and
    R4 is hydroxyl, carboxyl, methoxycarbonyl or aminocarbonyl,
and the salts of these compounds.

Particularly preferred compounds of the formula I are those in which
  R1 is methoxy,
  R2 is methyl or isopropyl,
  R3 is cyano,
  A is B, —CH(R4)— or >C=O,
    B is oxygen (—O—) and
    R4 is hydroxyl, carboxyl, methoxycarbonyl or aminocarbonyl,
and the salts of these compounds.

One embodiment of the particularly preferred compounds of the formula I are those in which
  R1 is methoxy,
  R2 is methyl or isopropyl,
  R3 is cyano,
  A is oxygen (—O—),
and the salts of these compounds.

The compounds of the formula I can be present—if A is —CH(R4)— as cis or trans isomers. The invention therefore includes both all pure cis and trans isomers and their mixtures in any mixing ratio. The pure cis isomers are preferred in this connection.

The invention further relates to processes for the preparation of the compounds of the formula I and their salts.

Compounds of the formula I in which A is —CH(R4)—, R1, R2 and R3 have the meanings indicated above and R4 is carboxyl can be prepared, for example, by hydrolyzing corresponding compounds of the formula I in which, is —CH(R4)— and R4 is alkoxycarbonyl and, if desired, then converting compounds of the formula I obtained into their salts, or converting salts of the compounds of the formula I obtained into the free compounds.

If desired, further compounds of the formula I can be converted into other compounds of the formula I by derivatization (in particular of the radicals R3 and R4) in a manner known to the person skilled in the art. In this manner, for example, compounds of the formula I in which R1, R2 and R3 have the meanings indicated above, A is —CH(R4)— and R4 is aminocarbonyl, mono- or di-alkylaminocarbonyl, alkoxyaminocarbonyl or hydroxyaminocarbonyl, are also accessible.

The hydrolysis of compounds of the formula I in which A is —CH(R4)— and R4 is alkoxycarbonyl is carried out by application of methods known to the person skilled in the art.

Compounds of the formula I in which A is —CH(R4)—, R1, R2 and R3 have the meanings indicated above and R4 is alkoxycarbonyl are obtained, for example, by solvolysis of corresponding compounds of the formula I, in which A is

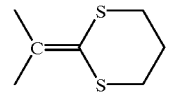

The solvolysis is preferentially carried out in an absolute alcohol as a solvent under acidic conditions in the presence of a mercury salt, such as, for example, mercury(II) chloride.

Compounds of the formula I, in which A is

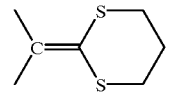

and R1, R2 and R3 have the meanings indicated above, can be prepared, for example, from the corresponding compounds of the formula II

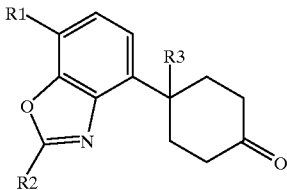

by reaction with 2-lithium-2-trimethylsilyl-1,3-dithiane.

The reaction is expediently carried out at low temperatures (preferably −60° to −100° C.) under a protective gas atmosphere in an inert solvent such as, for example, n-hexane, diethyl ether or tetrahydrofuran or mixtures thereof.

Compounds of the formula II in which R1 and R2 have the abovementioned meanings and R3 is cyano can be prepared, for example, by application of known methods starting from corresponding compounds of the formula III

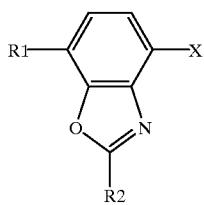

in which X is the group —CH₂CN, according to reaction scheme 1.

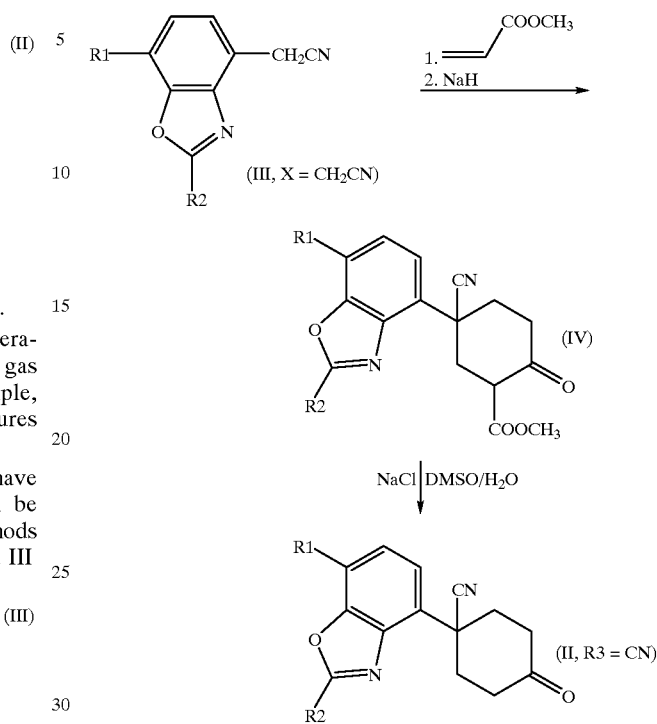

The compounds of the formula III in which R1 and R2 have the meanings indicated above and X is the group —CH₂CN can be prepared according to the general reaction scheme 2.

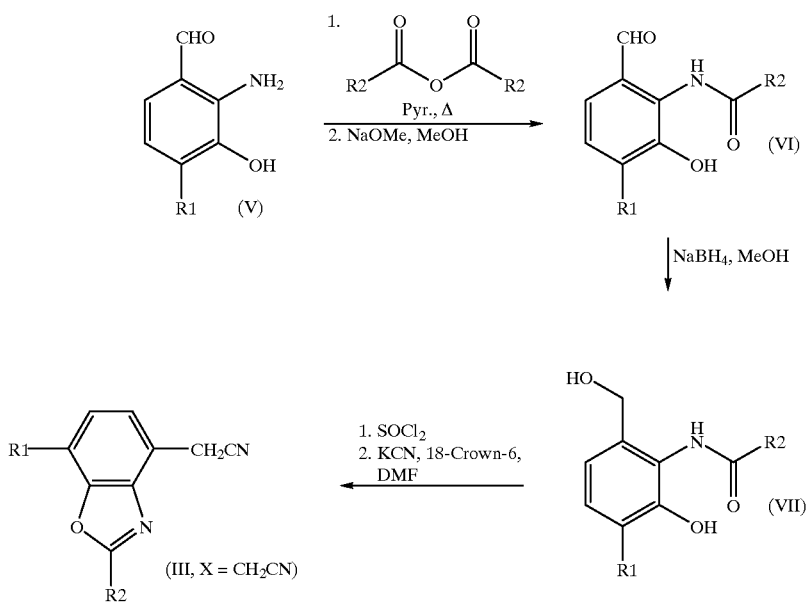

The synthesis of compounds of the formula III is described by way of example under "starting compounds". Further compounds can be prepared analogously.

The preparation of compounds of the formula V is described, for example, by M. Grossa, F. Wessely in Monatshefte Chemie 1966, 97, 1384–1390.

Compounds of the formula I in which R1 and R2 have the abovementioned meanings, R3 is hydrogen or cyano and A is —CH(OH)— can be prepared from corresponding compounds of the formula II by selective reduction of the carbonyl group.

The preparation of the keto compounds of the formula II in which R3 is cyano or hydrogen is described in reaction schemes 1 and 3.

skilled in the art, preferably in suitable inert solvents such as 1,2-dimethoxyethane or an alcohol such as methanol, using a suitable reductant such as, for example, sodium borohydride or lithium borohydride.

Compounds of the formula I in which R1 and R2 have the abovementioned meanings, R3 is cyano, nitro or 1–4C-alkoxycarbonyl and A is oxygen (—O—), imino (—NH—), sulfinyl (—S(O)—) or sulfonyl (—S(O)$_2$—) can be prepared, for example, from compounds of the formula III in which R1 and R2 have the meanings indicated above and X is —CH$_2$CN, —CH$_2$NO$_2$ or —CH$_2$COOR (R=1–4C-alkyl) by reaction with suitably activated ethers, amines, sulfines or sulfones.

An The reactions are preferably carried out in anhydrous inert solvents such as, for example, THF, DMF, DMSO or

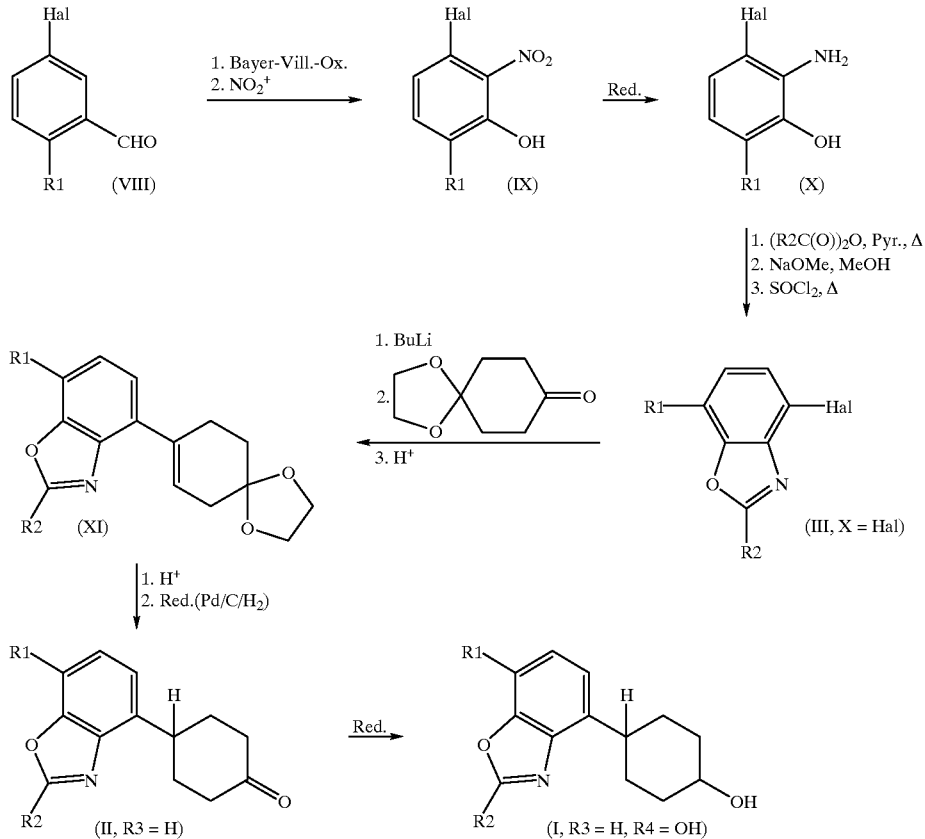

Reaction scheme 3

Compounds of the formula II in which R1 and R2 have the abovementioned meanings and R3 is hydrogen are accessible, for example, by addition of appropriate compounds of the formula III, in which X has the meaning lithium, to 1,4-cyclohexanedione, subsequent elimination of water and selective reduction of the resulting double bond. The 1,4-cyclohexanedione is expediently employed in partially protected form, for example as a monoethylene ketal, and the protective group is removed again after reaction has taken place (reaction scheme 3).

Compounds of the formula III in which X is lithium are accessible from corresponding compounds of the formula III in which X is halogen, in particular bromine, by metal-halogen exchange.

The reduction of the carbonyl group in compounds of the formula II is carried out in a manner known to the person HMPT or mixtures thereof and, depending on reactivity of the reagents employed, at temperatures between –30° C. and 100° C.

After deprotonation of the —CH$_2$CN, —CH$_2$NO$_2$ or the —CH$_2$COOR (R=1–4C-alkyl) group by a suitable base, ring formation is carried out by reaction with an ether, amine, sulfine or sulfone provided with suitable leaving groups. Suitable leaving groups which may be mentioned are halogen, in particular chlorine and bromine, and reactive esterified hydroxyl groups (e.g. the toluenesulfonyloxy group).

Suitably activated ethers (1), amines (2), sulfines (3) and sulfones (4) which suggest themselves are, for example, bis[2-(toluene-4-sulfonyloxy)ethyl]ether (1), N-benzyl-bis[2-(toluene-4-sulfonyloxy)-ethyl]amine (2), bis[2-(toluene-4-sulfonyloxy)ethyl]sulfine (3) and bis(2-chloroethyl) sulfone (4), (1) can be prepared according to C. Almensa, A. Moyano, F. Serratosa, Tetrahedron 1992, 48, 1497–1506, (2) or (3) can be prepared from the corresponding bis-hydroxyl compounds, N-benzyl-bis(2-hydroxyethyl)-amine (Mamaew, Schischkin, J. Org. Chem. (USSR), engl. Transl. 1966, 2, 584) or bis(2-hydroxyethyl) sulfine (Price, Bullit, J. Org. Chem. 1947, 12, 277) by ditosylation.

The protective group of the amine (2) temporarily introduced can be removed again after ring formation has taken place. Bis(2-chloroethyl) sulfone (4) is commercially obtainable.

Compounds of the formula III in which R1 and R2 have the meanings indicated above and X is —$CH_2COOR$ can be prepared, for example, by hydrolysis and subsequent esterification of the corresponding compounds of the formula III in which X is —$CH_2CN$.

The preparation of compounds of the formula III in which X is —$CH_2NO_2$ is described, for example, in J. Organic Chemistry, 1988, 53, 2872–2873.

Compounds of the formula I in which R1 and R2 have the meanings indicated above, R3 is 1–4C-alkoxy and A is oxygen (—O—) can be obtained from the corresponding compounds of the formula I in which R3 is hydroxyl by reaction with suitable alkylating agents.

Compounds of the formula I in which R1 and R2 have the meanings indicated above, R3 is hydroxyl and A is oxygen (—O—) can be obtained, for example, from compounds of the formula III in which R1 and R2 have the meanings indicated above and X is lithium by reaction with tetrahydropyran-4-one.

Compounds of the formula I in which R1, R2 and R3 have the meanings indicated above, A is >C=N—R5 and R5 is hydroxyl can be obtained by reaction of the corresponding compounds of the formula II with hydroxylamine.

By means of further derivatizations of these oxime compounds known to the person skilled in the art on the basis of his/her expert knowledge, those compounds of the formula I in which A is carbonylimino (by Beckmann rearrangement of the corresponding oxime compounds) or in which A is >C=N—R5 and R5 is 1–4C-alkylcarbonyloxy (by acylation of the corresponding oxime compounds) are also accessible.

It is known to the person skilled in the art that it can be necessary in the case of a number of reactive centers on a starting or intermediate compound to block one or more reactive centers temporarily by protective groups in order to allow a reaction to proceed specifically at the desired reaction center. A detailed description of the use of a large number of proven protective groups is found, for example, in T. W. Greene, Protective Groups in Organic Synthesis, John Wiley & Sons, 1991.

The substances according to the invention are isolated and purified in a manner known per se, e.g. by distilling off the solvent in vacuo and recrystallizing the resulting residue from a suitable solvent or subjecting it to one of the customary purification methods, such as, for example, column chromatography on suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low molecular weight aliphatic alcohol such as ethanol or isopropanol), which contains the desired acid or base, or to which the desired acid or base is then added.

The salts are obtained by filtering, reprecipitating, precipitating with a nonsolvent for the addition salt or by evaporating the solvent. Salts obtained can be converted by alkalization or by acidification into the free compounds, which in turn can be converted into salts. In this manner, pharmacologically intolerable salts can be converted into pharmacologically tolerable salts.

The following examples serve to illustrate the invention in greater detail without restricting it. Further compounds of the formula I, whose preparation is not described explicitly, can also be prepared in an analogous manner or in a manner familiar to the person skilled in the art per se using customary process techniques.

The abbreviation h stands for hour(s), min. for minute(s), RT for room temperature, m.p. for melting point, DMSO for dimethyl sulfoxide, DMF for dimethylformamide, THF for tetrahydrofuran, HMPT far hexamethylphosphoramide, LDA for lithium diisopropylamide and TLC for thin-layer chromatography.

EXAMPLES

FINAL PRODUCTS 1. 4a-Cyano-4e-(2-methyl-7-methoxybenzoxazol-4-yl)tetrahydropyran 500 mg (2.47 mmol) of 2-methyl-7-methoxybenzoxazol-4-ylacetonitrile (starting compound A3) are dissolved in 25 ml of absolute THF at RT. 7 ml of HMPT are then added and the solution is cooled to −30° C. under a protective gas atmosphere. Freshly prepared LDA (0.86 ml of diisopropylamine and 4.18 ml of a 1.6 M n-butyllithium solution in n-hexane) in 5 ml of absolute THF is then slowly added dropwise to the reaction solution by means of a dropping funnel cooled with dry ice. The mixture is stirred at −30° C. for a further 30 min. After gentle warming of the reaction solution to −20° C., a solution of bis[2-(toluene-4-sulfonyloxy)ethyl] ether (1.55 g, 3.73 mmol) [ref. C. Almensa, A. Moyano, F. Serratosa, Tetrahedron 1992, 48, 1497–1506] in 5 ml of absolute THF is then slowly injected into the reaction solution under a nitrogen countercurrent (–>deep-red coloration of the reaction solution). The reaction solution is then slowly warmed to about 0° C. and the end of reaction is checked by means of thin-layer chromatography, The reaction solution is poured onto a half-concentrated ammonium chloride solution and extracted 5 times with ethyl acetate. The combined organic phases are dried over $MgSO_4$ and concentrated in vacuo. The crude product is purified by chromatography on silica gel (petroleum ether/ethyl acetate; 8:2). After recrystallizing from petroleum ether/ethyl acetate, the title compound is obtained as colorless crystals (130 mg). TLC (silica gel, petroleum ether/ethyl acetate, 6:4); $R_f$–0.40, m.p. 72° C.

2. 4a-Cyano-4e-(2-isopropyl-7-methoxybenzoxazol-4-yl)-tetrahydropyran 550 mg (2.39 mmol) of 2-isopropyl-7-methoxybenzoxazol-4-ylacetonitrile (starting compound A6) are dissolved in 25 ml of absolute THF at RT. 7 ml of HMPT are then added and the solution is cooled to −30° C. under a protective gas atmosphere. Freshly prepared LDA (0.83 ml of diisopropylamine and 4.05 ml of a 1.6 M n-butyllithium solution in n-hexane) in 5 ml of absolute THF is then slowly added dropwise to the reaction solution by means of a dropping funnel cooled with dry ice. The mixture is stirred at −30° C. for a further 30 min. After gentle warming of the reaction solution to −20° C., a solution of bis[2-(toluene-4-sulfonyloxy)ethyl]ether (1.50 g, 3.61 mmol) [ref. C Almensa, A. Moyano, F. Serratosa, Tetrahedron 1992, 48, 1497–1506] in 5 ml of absolute THF is slowly injected into the reaction solution under a nitrogen countercurrent (–>deep-red coloration of the reaction solution). The reaction solution is then slowly warmed to about 0° C. and the end of reaction is checked by means of thin-layer chromatography. The reaction solution is poured onto a half-concentrated ammonium chloride solution and extracted 5 times with ethyl acetate. The combined organic phases are dried over $MgSO_4$ and concentrated in vacuo. The crude product is purified by chromatography on silica gel (petroleum ether/ethyl acetate: 9:1). After recrystallizing from petroleum ether/ethyl acetate, the title compound is obtained as colorless crystals (220 mg). TLC (silica gel, petroleum ether/ethyl acetate, 7:3); $R_f$=0.39, m.p. 156.5° C.

3. 4-Cyano-4-(2-isopropyl-7-methoxybenzoxazol-4-yl)cyclohexanone 0.69 g (1.86 mmol) of methyl 5-cyano-5-(2-isopropyl-7-methoxybenzoxazol-4-yl)-2-oxocyclohexanecarboxylate (starting compound A8) is dissolved in 16 ml of DMSO, a solution of 0.73 g of NaCl in 2 ml of dist. water is added and the mixture is stirred at 140° C. for 8.5 h. After cooling the reaction mixture, it is diluted with 80 ml of dist. water and extracted with ethyl acetate, and the organic phase is separated off, dried over magnesium sulfate and concentrated to dryness in vacuo. After chromatography, the title compound (0.45 g) is obtained as a colorless solid. TLC, silica gel (glass plates), petroleum ether/ethyl acetate (7:3), $R_f$=0.56, m.p. 118° C.

4. cis-4-Cyano-4-(2-isopropyl-7-methoxybenzoxazol-4-yl)cyclohexan-1-ol

Sodium borohydride (0.16 g, 4.0 mmol) is introduced with stirring at RT into a solution of the compound (0.5 g, 1.6 mmol) prepared according to procedure 3 in absolute methanol (37 ml). The suspension is stirred at RT for 2 h. The reaction mixture is then treated with 1N hydrochloric acid until a pH of 3 is obtained. Distilled water (75 ml) is added to the reaction solution and it is extracted with ethyl acetate (60 ml, 3 times). The combined organic phases are dried over magnesium sulfate and, after filtration, concentrated in vacuo. After chromatography, the title compound (0.5 g) is obtained as colorless crystals. TLC, silica gel (glass plates), petroleum ether/ethyl acetate (6:4), $R_f$=0.17, m.p. 116.5° C.

5. Methyl cis-4-cyano-(2-isopropyl-7-methoxybenzoxazol-4-yl)cyclohexane-1-carboxylate The dithiane compound (1.7 g, 4.1 mmol) prepared according to procedure A9 is dissolved in absolute methanol (78 ml) together with mercury(II) chloride (4.6 g, 16.9 mmol) and treated with perchloric acid (70% strength, 3.8 ml). The mixture is heated under reflux for about 1 h. After cooling to RT, the reaction mixture is filtered off with suction through kieselguhr. The filtrate is diluted with ethyl acetate (100 ml) and washed with half-concentrated $NaHCO_3$ solution (100 ml). The organic phase is further extracted with $Na_2SO_3$ solution (40% strength, 100 ml), dried over magnesium sulfate, filtered and concentrated in vacuo. Further purification is carried out by means of chromatography and yields the title compound (0.59 g) as a colorless solid. TLC, silica gel (glass plates), petroleum ether/ethyl acetate (7:3), $R_f$=0.51, m.p. 83° C.

6. cis-4-Cyano-4-(2-isopropyl-7-methoxybenzoxazol-4-yl)cyclohexane-1-carboxylic acid The cis-carboxylic acid methyl ester compound (0.49 g, 1.37 mmol) prepared according to procedure 5 is dissolved in a mixture of methanol (21 ml) and ethanol (14 ml) and treated with an aqueous KOH solution (0.63 g of KOH in 7 ml of water) at RT with stirring. It is stirred overnight at RT. The reaction solution is then almost completely concentrated in vacuo. The residue is taken up in 1N hydrochloric acid (20 ml) and extracted (3 times) with dichloromethane (30 ml). The combined organic phases are dried over magnesium sulfate, filtered off and concentrated in vacuo. The title compound (0.4 g) is obtained as colorless crystals. TLC, silica gel (glass plates), petroleum ether/ethyl acetate (6:4), $R_f$=0.10, m.p. 217.5° C.

7. Cis-4-Cyano-4-(2-isopropyl-7-methoxybenzoxazol-4-yl)cyclohexane-1-carboxamide The cis-carboxylic acid compound (0.4 g, 1.17 mmol) prepared according to procedure 6 is dissolved in thionyl chloride (5.2 ml) and stirred under reflux for 1 h. The reaction solution is concentrated in vacuo and coevaporated with toluene (2 times). The residue obtained is dissolved in absolute toluene (10 ml) and cooled to 0° C. Ammonia gas is subsequently passed through the solution for 10 min., then diethyl ether (10 ml) is added. The resulting colorless precipitate is filtered off and washed with diethyl ether (10 ml). The title compound (0.31 g) is obtained as colorless crystals. TLC, silica gel (glass plates), dichloromethane/methanol 1(9:1), $R_f$=0.55, m.p. 228° C.

Starting Compounds

A1. 2-Acetamido-3-hydroxy-4-methoxybenzaldehyde

2-Amino-3-hydroxy-4-methoxybenzaldehyde (20.0 g, 0.12 mol) [M. Grossa, F. Wessely *Monatsh. Chem.* 1966, 97, 1384–1390] is dissolved at RT in a mixture of pyridine (250 ml) and acetic anhydride (250 ml). The solution is warmed to 60° C. and stirred for 1.5 h. The reaction solution is then poured onto a mixture of ice and half-concentrated aqueous NaCl solution (1:1), extracted with ethyl acetate (5 times), dried over $MgSO_4$, filtered off and concentrated in vacuo. The title compound is obtained as a slightly yellow solid (12.5 g) after silica gel chromatography [petroleum ether/ethyl acetate (7:3)]. TLC, silica gel (glass plates), petroleum ether/ethyl acetate (7:3), $R_f$=0.23.

A2. 2-Acetamido-3-hydroxy-4-methoxybenzyl Alcohol $NaBH_4$ (550 mg, 14.53 mmol) is slowly added to a solution of 2-acetamido-3-hydroxy-4-methoxybenzaldehyde (3.0 g, 14.34 mmol) [M. Grossa, F. Wessely *Monatsh. Chem.* 1966, 97, 1384–1390] in methanol (80 ml). After stirring for 10 minutes, the suspension is poured onto a 0.1 N aqueous HCl solution (50 ml) and then extracted with $CH_2Cl_2$ (3 times). The organic phases are combined, dried over $MgSO_4$, filtered off and concentrated in vacuo. The residue obtained is purified by means of chromatography with pure ethyl acetate and yields the title compound as a colorless solid (2.2 g). TLC, silica gel (glass plates), ethyl acetate, $R_f$=0.19.

A3. 2-Methyl-7-methoxybenzoxazol-4-ylacetonitrile

Thionyl chloride (40 ml) is slowly added at 0° C. with stirring to a suspension of 2-acetamido-3-hydroxy-4-methoxybenzyl alcohol (2.5 g, 12.0 mmol) and anhydrous $CH_2Cl_2$ (30 ml). After the reaction mixture has warmed to RT, it is stirred for 1 h and then stirred at 50° C. for a further 1.5 h. The reaction solution is concentrated in vacuo and then coevaporated with toluene (3 times). The residue obtained is dissolved in a mixture of toluene and DMF (8:1, 45 ml) and added dropwise to a solution of KCN (1.0 g, 15.4 mmol) in 18-crown-6 (4.07 g, 15.4 mmol) and absolute DMF (55 ml). The reaction solution is stirred overnight at RT and then poured into a half-concentrated aqueous NaCl solution, extracted with ethyl acetate (5 times), dried over MgSO$_4$, filtered off and concentrated in vacuo. For further purification, the crude product is filtered through a silica gel column [petroleum ether/ethyl acetate (6:4)]. The title compound is obtained as colorless crystals (1.28 g). TLC, silica gel (glass plates), petroleum ether/ethyl acetate (6:4), R$_f$=0.32.

A4. 2-Isopropylamido-3-hydroxy-4-methoxybenzaidehyde

2-Amino-3-hydroxy-4-methoxybenzaldehyde (3.0 g, 17.95 mmol) is dissolved at RT in a mixture of pyridine (50 ml) and isobutyric anhydride (50 ml). The solution is stirred at 100° C. for 1.5 h. The reaction solution is then poured onto a mixture of ice and half-concentrated aqueous NaCl solution (1:1), extracted with ethyl acetate (5 times), dried over MgSO$_4$, filtered off and concentrated in vacuo. The 2-isopropylamido-3-isopropylcarbonyloxy-4-methoxybenzaldehyde obtained is dissolved in absolute methanol (80 ml) and stirred at RT for 1 h with sodium methoxide (14.6 ml of a 5.5 molar solution in absolute methanol). The reaction solution is then poured onto a half-concentrated aqueous ammonium chloride solution, extracted with ethyl acetate (5 times), dried over MgSO$_4$, filtered off and concentrated in vacuo. The title compound is obtained after silica gel chromatography [petroleum ether/ethyl acetate (7:3)] as a slightly yellow solid (920 mg). TLC, silica gel (glass plates), petroleum ether/ethyl acetate (7:3), R$_f$=0.39.

A5. 2-Isopropylamido-3-hydroxy4-methoxybenzyl alcohol

NaBH$_4$ (145 mg, 3.83 mmol) is slowly added to a solution of 2-isopropylamido-3-hydroxy-4-methoxybenzaldehyde (900 mg, 3.79 mmol) in methanol (25 ml). After stirring for 10 minutes, the suspension is poured onto a 0.1 N aqueous HCl solution (20 ml) and then extracted with CH$_2$Cl$_2$ (3 times). The organic phases are combined, dried over MgSO$_4$, filtered off and concentrated in vacuo. The residue obtained is purified by means of chromatography with petroleum ether/ethyl acetate (6:4). The title compound is obtained as a colorless solid (820 mg). TLC, silica gel (glass plates), petroleum ether/ethyl acetate (6.4), R$_f$=0.30.

A6. 2-Isopropyl-7-methoxybenzoxazol-4-ylacetonitrile

Thionyl chloride (12 ml) is slowly added at 0° C. with stirring to a suspension of 2-isopropylamido-3-hydroxy-4-methoxybenzyl alcohol (800 mg, 3.34 mmol) and anhydrous CH$_2$Cl$_2$ (9 ml). After the reaction mixture has warmed to RT, it is stirred for 1 h and then stirred at 50° C. for a further 2 h. The reaction solution is concentrated in vacuo and then coevaporated with toluene (3 times). The residue obtained is dissolved in DMF (15 ml) and added dropwise to a solution of KCN (282 mg, 4.34 mmol) in 18-crown-6 (1.15 g, 4.34 mmol) and absolute DMF (15 ml). The reaction solution is stirred overnight at RT and then poured into a half-concentrated aqueous NaCl solution, extracted with ethyl acetate (5 times), dried over MgSO$_4$, filtered off and concentrated in vacuo. For further purification, the crude product is filtered through a silica gel column [petroleum ether/ethyl acetate (7:3)]. The title compound is obtained as colorless crystals (550 mg). TLC, silica gel (glass plates), petroleum ether/ethyl acetate (7:3), R$_f$=0.50.

A7. Methyl 4-cyano-4-(2-isopropyl-7-methoxybenzoxazol-4-yl)heptane-1,7-dicarboxylate A solution of 0.65 g (2.82 mmol) of 2-isopropyl-7-methoxybenzoxazol-4-ylacetonitrile and 0.13 ml of Triton B in 17 ml of absolute tetrahydrofuran is warmed to 65° C. for 10 min and 2.45 ml (31.4 mmol) of methyl acrylate are then added dropwise at 45° C. The solution is heated to reflux for 2 h. After cooling, the solvent is concentrated in vacuo, and the residue is taken up in 30 ml of ethyl acetate and extracted with half-saturated sodium chloride solution. The organic phase is dried over magnesium sulfate and concentrated in vacuo. Column chromatography affords the title compound (0.75 g) as a colorless oil. TLC, silica gel (glass plates), petroleum ether/ethyl acetate (8:2), R$_f$=0.54.

A8. Methyl 5-cyano-5-(2-isopropyl-7-methoxybenzoxazol-4-yl)-2-oxocyclohexanecarboxylate 0.21 g (5.20 mmol) of sodium hydride (60% strength in paraffin) is added to a solution of 0.75 9 (1.86 mmol) of the compound prepared according to procedure A7 in 18 ml of 1,2-dimethoxyethane and the mixture is stirred under reflux for 2 h. It is then allowed to cool to RT, 2 ml of methanol and then 5 ml of 1N hydrochloric acid are added, and the mixture is then treated with 50 ml of distilled water and extracted with ethyl acetate. The organic phases are combined, dried over magnesium sulfate and concentrated to dryness in vacuo. The title compound (0.69 g) is obtained as colorless crystals by column chromatography. TLC, silica gel (glass plates), petroleum ether/ethyl acetate (8:2), R$_f$=0.46, m.p. 150° C.

A9.1-(2-Isopropyl-7-methoxybenzoxazol-4-yl)-4-[1,3] dithian-2-ylidenecyclohexanecarbonitrile 2-Trimethylsilyl-1,3-dithiane (2.1 ml, 11.01 mmol) is dissolved in absolute THF (56 ml) and cooled to −70° C. with stirring. A solution of n-butyllithium in n-hexane (6.9 ml, 11.1 mmol of a 1.6 molar solution) is then slowly added dropwise under a nitrogen atmosphere by means of a glass syringe and the mixture is stirred at −45° C. for a further 30 min. After cooling to −70° C. again, a solution of 4-cyano-4-(2-isopropyl-7-methoxybenzoxazol-4-yl)cyclohexanone (1.5 g, 4.80 mmol, compound 3) in absolute THE (33 ml) is slowly added dropwise. The mixture is stirred at −70° C. for 1 h and then slowly warmed to RT (about 2 h). For working-up, the reaction solution is diluted with ethyl acetate (80 ml) and extracted (2 times) with 0.1 N hydrochloric acid (80 ml). The organic phase is dried using magnesium sulfate, filtered off and concentrated in vacuo. Column chromatography affords the title compound (1.34 9) as a colorless solid. TLC, silica gel (glass plates), petroleum ether/ethyl acetate (85:15), R$_f$=0.6.

Commercial Utility

The compounds according to the invention have valuable pharmacological properties which make them commercially utilizable. As selective cyclic nucleotide phosphodiesterase (PDE) inhibitors (namely of type 4), they are suitable, on the one hand, as bronchial therapeutics (for the treatment of airway obstructions on account of their dilating but also on account of their respiratory rate- or respiratory drive-increasing action) and for the elimination of erectile dysfunction on account of the vasodilating action, but on the other hand especially for the treatment of disorders, in particular of inflammatory nature, e.g. of the airways (asthma prophylaxis), of the skin, of the central nervous system, of the intestine, of the eyes and of the joints, which are mediated by mediators such as histamine, PAF (plate-activating factor), arachidonic acid derivatives such as leukotrienes and prostaglandins, cytokines, interleukins, chemokines, alpha-, beta- and gamma-interferon, tumor necrosis factor (TNF) or oxygen radicals and proteases. In this context, the compounds according to the invention are distinguished by a low toxicity, a good enteral absorption (high bioavailability), a wide therapeutic breadth and the absence of significant side effects.

On account of their PDE-inhibiting properties, the compounds according to the invention can be employed as therapeutics in human and veterinary medicine, where they can be used, for example, for the treatment and prophylaxis of the following diseases: acute and chronic (in particular inflammatory and allergen-induced) airway disorders of various origin (bronchitis, allergic bronchitis, bronchial asthma, emphysema, COPD); dermatoses (especially of proliferative, inflammatory and allergic nature) such as, for example, psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and wide-area pyodermias, endogenous and exogenous acne, acne rosacea and other proliferative, inflammatory and allergic skin disorders; disorders which are based on an excessive release of TNF and leukotrienes, i.e., for example, disorders of the arthritis type (rheumatoid arthritis, rheumatoid spondylitis, osteoarthritis and other arthritic conditions), disorders of the immune system (AIDS, multiple sclerosis), graft versus host reactions, transplant rejection reactions, symptoms of shock [septic shock, endotoxin shock, Gram-negative sepsis, toxic shock syndrome and ARDS (adult respiratory distress syndrome)] and also generalized inflammations in the gastrointestinal area (Crohn's disease and ulcerative colitis); disorders which are based on allergic and/or chronic, faulty immunological reactions in the area of the upper airways (pharynx, nose) and the adjacent regions (paranasal sinuses, eyes), such as, for example, allergic rhinitis/sinusitis, chronic rhinitis/sinusitis, allergic conjunctivitis and also nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and of the ureters in connection with kidney stones. In addition, the compounds according to the invention can be employed for the treatment of diabetes insipidus and disorders in connection with disturbances of the brain metabolism, such as, for example, cerebral senility, senile dementia (Alzheimer's dementia), multiinfarct dementia or alternatively disorders of the CNS, such as, for example, depressions or arteriosclerotic dementia.

A further subject of the invention is a process for the treatment of mammals, including humans, that are suffering from one of the abovementioned diseases. The process comprises administering to the sick mammal a therapeutically efficacious and pharmacologically tolerable amount of one or more of the compounds according to the invention.

A further subject of the invention are the compounds according to the invention for use in the treatment and/or prophylaxis of diseases, in particular of the diseases mentioned.

The invention likewise relates to the use of the compounds according to the invention for the production of medicaments which are employed for the treatment and/or prophylaxis of the diseases mentioned.

Medicaments for the treatment and/or prophylaxis of the diseases mentioned, which contain one or more of the compounds according to the invention, are furthermore a subject of the invention.

A further subject of the invention is a commercial product consisting of a customary secondary packaging, a primary packaging containing the medicament (for example an ampoule or a blister pack) and, if desired, an enclosed leaflet, the medicament showing antagonistic action against cyclic neocleotide phosphodiesterases of type 4 (PDE4) and leading to the lessening of the symptoms of diseases which are connected with cyclic nucleotide phosphodiesterases of type 4, and the suitability of the medicament for the prophylaxis or treatment of diseases which are connected with cyclic nucleotide phosphodiesterases of type 4 being indicated on the secondary packaging and/or on the enclosed leaflet of the commercial product, and the medicament containing one or more compounds of the formula I according to the invention. The secondary packaging, the primary packaging containing the medicament and the included leaflet otherwise correspond to what the person skilled in the art would regard as standard for medicaments of this type.

The medicaments are prepared by processes known per se and familiar to the person skilled in the art. As medicaments, the compounds according to the invention (=active compounds) are either used as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

Auxiliaries which are suitable for the desired pharmaceutical formulations are familiar to the person skilled in the art on the basis of his/her expert knowledge. In addition to solvents, gel-forming agents, ointment bases and other active compound excipients, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this, these are either administered directly as a powder (preferably in micronized form) or by nebulization of solutions or suspensions which contain them. With respect to the preparations and administration forms, reference is made, for example, to the details in European Patent 163 965.

For the treatment of dermatoses, the compounds according to the invention are in particular administered in the form of those medicaments which are suitable for topical application. For the production of the medicaments, the compounds according to the invention (=active compounds) are preferably mixed with suitable pharmaceutical auxiliaries and processed further to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are produced by processes known per se. The dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.03 and 3 mg per kilogram per day.

Biological Investigations

In the investigation of PDE4 inhibition at the cellular level, the activation of inflammatory cells is of particular importance. An example which may be mentioned is the FMLP (N-formyl-methionyl-leucyl-phenyl-alanine)-induced superoxide production of neutrophilic granulocytes, which can be measured as luminol-potentiated chemiluminescence [Mc Phail L C, Strum S L, Leone P A and Sozzani S, The neutrophil respiratory burst mechanism. In "Immunology Series" 1992, 57, 47–76; ed. Coffey R G (Marcel Decker, Inc., New York-Basel-Hong Kong)].

Substances which inhibit chemiluminescence and cytokine secretion and the secretion of proinflammatory mediators in inflammatory cells, in particular neutrophilic and eosinophilic granulocytes, T lymphocytes, monocytes and macrophages, are those which inhibit PDE4. This isoenzyme of the phosphodiesterase families is particularly represented in granulocytes. Its inhibition leads to the increase of the intracellular cyclic AMP concentration and thus to the inhibition of cellular activation. PDE4 inhibition by the substances according to the invention is thus a central indicator of the suppression in inflammatory processes. (Giembycz M A, Could isoenzyme-selective phosphodiesterase inhibitors render bronchodilatory therapy redundant in the treatment of bronchial asthma? Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE 3/4 inhibitor. In "New Drugs for Asthma Therapy", 379–402, Birkhäuser Verlag Basel 1991; Schudt C et al., Influence of selective phosphodiesterase inhibitors on human neutrophil functions and levels of cAMP and Ca; Naunyn-Schmiedebergs Arch Pharmacol 1991, 344, 682–690; Tenor H and Schudt C, Analysis of PDE isoenzyme profiles in cells and tissues by pharmacological methods. In "Phosphodiesterase Inhibitors", 21–40, "The Handbook of Immunopharmacology", Academic Press, 1996; Hatzelmann A et al., Enzymatic and functional aspects of dual-selective PDE3I4-inhibitors. In "Phosphodiesterase Inhibitors", 147–160, "The Handbook of Immunopharmacology, Academic Press, 1996.)

Inhibition of PDE4 Activity

Methodology

The activity test was carried out according to the method of Bauer and Schwabe, which was adapted to microtiter plates (Naunyn-Schmiedeberg's Arch. Pharmacol. 1980, 311, 193–198). In this test, the PDE reaction takes place in the first step. In a second step, the resulting 5'-nucleotide is cleaved by a 5'-nucleotidase of the snake venom from Crotalus atrox to give the uncharged nucleoside. In the third step, the nucleoside is separated from the remaining charged substrate on ion-exchange columns. The columns are eluted directly into minivials to which 2 ml of scintillator fluid is additionally added for counting 2 ml of 30 mM ammonium formate (pH 6.0).

The inhibitory values determined for the compounds according to the invention [inhibitory concentration as -log $IC_{50}$ (mol/l)] results from the following Table A, in which the numbers of the compounds correspond to the numbers of the examples.

TABLE A

Inhibition of the PDE4 activity

| Compound | -log $IC_{50}$ |
|---|---|
| 1 | 6.87 |
| 2 | 7.86 |
| 3 | 6.96 |
| 4 | 7.77 |
| 5 | 6.46 |
| 6 | 7.69 |
| 7 | 7.65 |

What is claimed is:

1. A compound of formula I

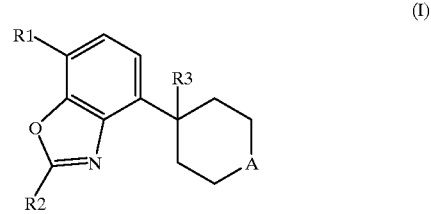

in which

R1 is 1–6C-alkoxy, 3–7C-cycloalkoxy, 3–7C-cycloalkylmethoxy, benzyloxy or completely or predominantly fluorine-substituted 1–4C-alkoxy, R2 is hydrogen, 1–7C-alkyl, 3–7C-cycloalkyl, 3–7C-cycloalkylmethyl or 1–4C-alkoxy-1–4C-alkyl, R3 is hydrogen, hydroxyl, nitro, cyano, ethynyl, carboxyl, 1–4C-alkoxy or 1–4C-alkoxycarbonyl, A is B, —CH(R4)—, >C=O or >C=N—R5, where B is oxygen (—O—), imino (—NH—), sulfinyl (—S(O)—), sulfonyl (—S(O)$_2$—) or carbonylimino (—C(O)NH—) and R4 is hydroxyl, carboxyl, 1–4C-alkoxycarbonyl, aminocarbonyl, mono- or di-1–4C-alkylaminocarbonyl, hydroxyaminocarbonyl (—C(O)NHOH) or 1–4C-alkoxyaminocarbonyl, R5 is hydroxyl or 1–4C-alkylcarbonyloxy, or a salt thereof.

2. A compound of formula I as claimed in claim 1, in which

R1 is 1–4C-alkoxy, 3–5C-cycdoalkoxy or completely or predominantly fluorine-substituted 1–2C-alkoxy, R2 is 1–4C-alkyl, 3–5C-cycloalkyl, 3–5C-cycloalkylmethyl or 1–2C-alkoxy-1–2C-alkyl, R3 is hydroxyl, cyano, carboxyl, 1–2C-alkoxy or 1–2C-alkoxycarbonyl, A is B, —CH(R4)—, >C=O or >C=N—R5, where B is oxygen (—O—), sulfinyl (—S(O)—), sulfonyl (—S(O)$_2$—) or carbonylimino (—C(O)N H—) and R4 is hydroxyl, carboxyl, 1–4C-alkoxycarbonyl or aminocarbonyl, R5 is hydroxyl or 1–4C-alkyicarbonyloxy, or a salt thereof.

3. A compound of formula I as claimed in claim 1, in which

R1 is 1–4C-alkoxy,

R2 is 1–4C-alkyl or 3–5C-cycloalkyl,

R3 is hydroxyl, cyano or methoxy,

A is B, —CH(R4)— or >C=O, where

B is oxygen (—O—) or sulfonyl (—S(O)$_2$—),

R4 is hydroxyl, carboxyl, methoxycarbonyl or aminocarbonyl, or a salt thereof.

4. A compound of formula I as claimed in claim 1, in which

R1 is 1–4C-alkoxy,
R2 is 1–4C-alkyl,
R3 is cyano,
A is B, —CH(R4)— or >C=O, where
    B is oxygen (—O—) and
    R4 is hydroxyl, carboxyl, methoxycarbonyl or aminocarbonyl,
or a salt thereof.

5. A compound of formula I as claimed in claim 1, in which

R1 is methoxy,
R2 is methyl or isopropyl,
R3 is cyano,
A is B, —CH(R4)— or >C=O,
    B is oxygen (—O—) and
    R4 is hydroxyl, carboxyl, methoxycarbonyl or aminocarbonyl,
or a salt thereof.

6. A compound of formula I as claimed in claim 1, in which

R1 is methoxy,
R2 is methyl isopropyl,
R3 is cyano,
A is oxygen (—O—),
or a salt thereof.

7. A method of treating a condition amenable to treatment with a cyclic nucleotide phosphodiesterase (PDE) inhibitor of type 4 which comprises administering an effective amount of a compound of Formula 1 as claimed in claim 1 or a pharmaceutically acceptable salt thereof to a subject in need of such treatment.

8. A medicament composition comprising a compound as claimed in claim 1 or a pharmaceutically acceptable salt thereof together with a pharmaceutical auxiliary and/or excipient.

9. A method of compounding a medicament composition for treating an amenable airway disorder by combining a cyclic nucleotide phosphodiesterase (PDE) inhibitor of type 4 with a pharmaceutical auxiliary and/or excipient, wherein the PDE inhibitor is a compound as claimed in claim 1 or a pharmacologically acceptable salt thereof.

\* \* \* \* \*